United States Patent [19]

Maples et al.

[11] Patent Number: 5,342,754
[45] Date of Patent: * Aug. 30, 1994

[54] PRESERVED, NON-INFECTIOUS CONTROL CELL FOR USE IN THE IDENTIFICATION OF A DISEASE THROUGH BLOOD TESTING

[75] Inventors: John A. Maples, Davie; Robert H. Raynor, Miramar; Olavi Siiman, Davie; Melissa J. Stiglitz, North Miami Beach; Stephen F. Healy, Jr., Miami, all of Fla.

[73] Assignee: Coulter Corporation, Miami, Fla.

[ * ] Notice: The portion of the term of this patent subsequent to Oct. 22, 2008 has been disclaimed.

[21] Appl. No.: 944,678

[22] Filed: Sep. 14, 1992

[51] Int. Cl.⁵ .................. A01N 1/02; G01N 31/00
[52] U.S. Cl. ........................ 435/2; 424/534; 436/10
[58] Field of Search ............... 435/2; 424/534; 436/10

[56] References Cited

U.S. PATENT DOCUMENTS

| | | | |
|---|---|---|---|
| 4,489,162 | 12/1992 | Hawkins et al. | 436/10 |
| 4,867,908 | 9/1989 | Recktenwald et al. | 252/408.1 |
| 4,876,189 | 10/1989 | Schetters et al. | 435/7 |
| 5,106,744 | 4/1992 | Kass | 435/240.2 |

FOREIGN PATENT DOCUMENTS 206842  2/1984  Fed. Rep. of Germany .

*Primary Examiner*—Douglas W. Robinson
*Assistant Examiner*—S. Saucier
*Attorney, Agent, or Firm*—Myron C. Cass

[57] ABSTRACT

The invention describes the preparation of non-infectious control cells from normal, non-infectious, non-disease altered blood by depletion or augmentation of one or more cell types found in normal blood to reflect a specific disease state. The control cells so produced are preserved and thereafter reconstituted for use in immunological assays.

3 Claims, 8 Drawing Sheets

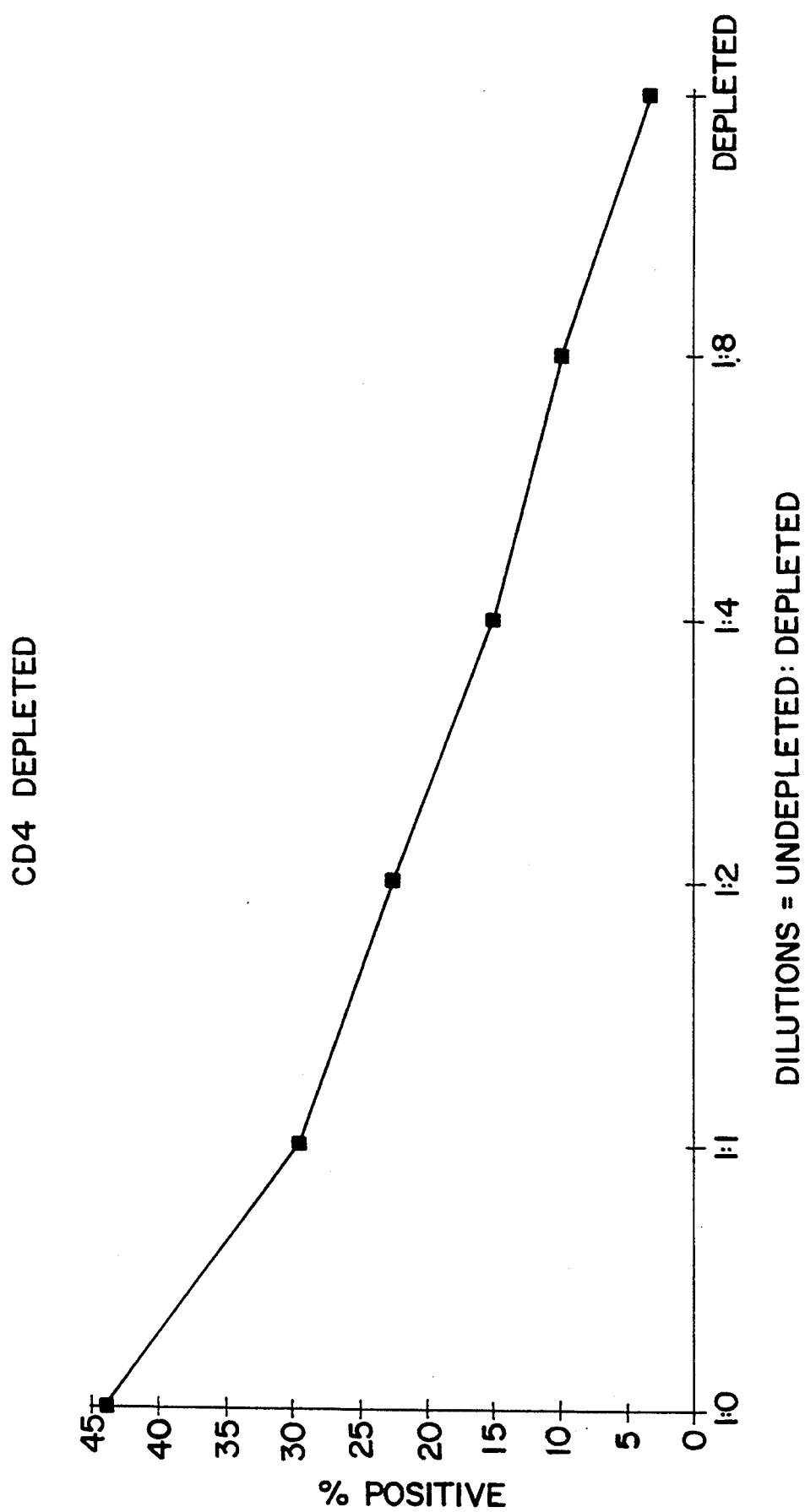

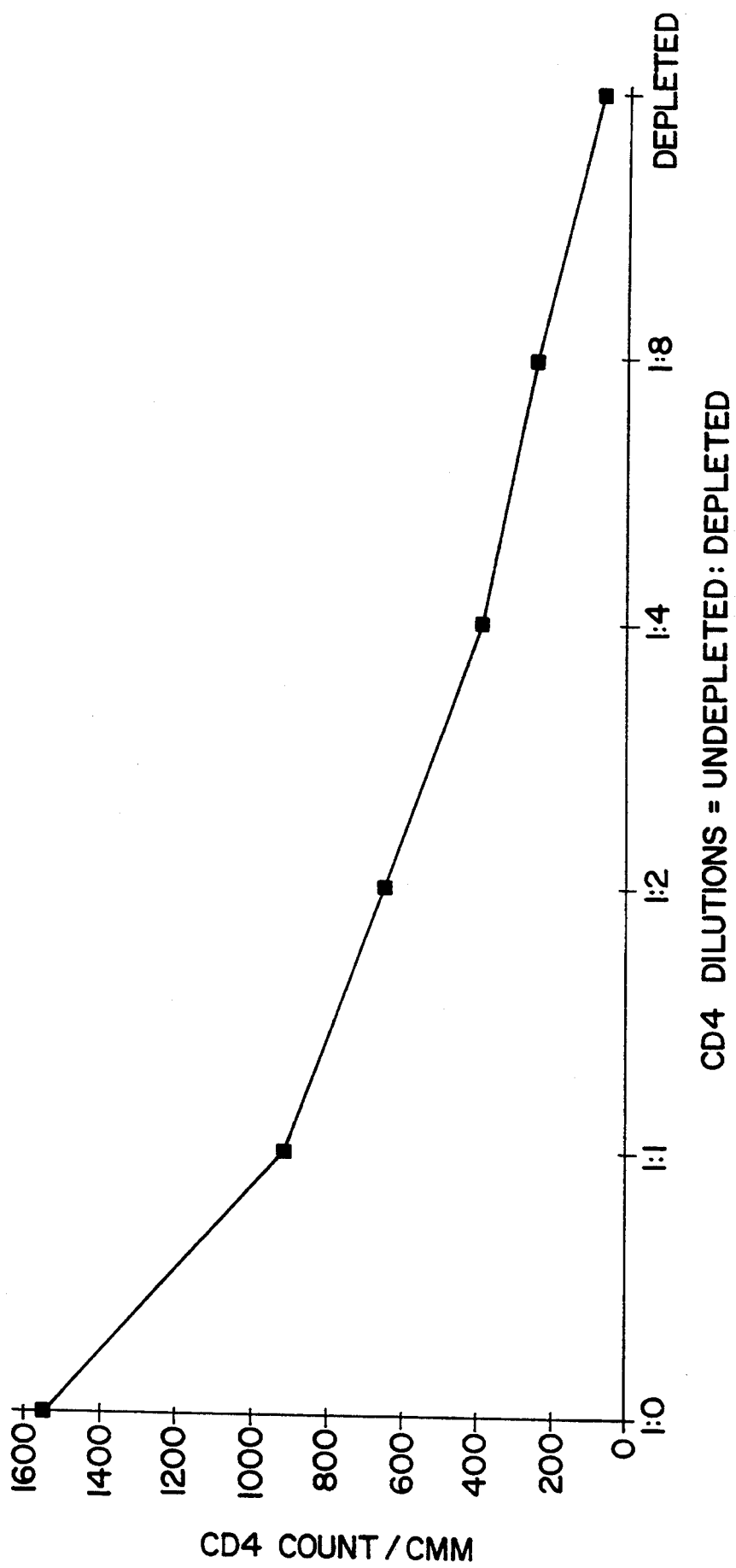

PRESERVED, NON-INFECTIOUS CONTROL CELL FOR USE IN THE IDENTIFICATION OF A DISEASE THROUGH BLOOD TESTING

RELATED INVENTION

This application is related to U.S. Pat. No. 5,059,518, issued Oct. 22, 1991. This application and U.S. Pat. No. 5,059,518 are owned by a common assignee, Coulter Corporation, Hialeah, Fla.

FIELD OF THE INVENTION

This invention relates to control cells and a method of producing the same for use in immunoassays. Specifically, this invention relates to preserved non-infectious control cells which have a population or count of at least one specific cell type that is indicative of the population or count of such cells in the blood or tissue sample of a mammal having a disease which results in a change in the count of such cells relative to their count in a normal blood or tissue sample. In particular, the non-infectious control cells are produced from normal, non-infectious, non-disease altered blood by the depletion or the augmentation of one or more cell types found in normal blood to reflect a specific disease state. The normal blood samples so depleted or augmented are then preserved, for example, by lyophilization, so as to have an extended storage life for subsequent application in clinical and immunological analytical procedures.

BACKGROUND OF THE INVENTION

Control cells are essential for the accuracy and precision of clinical and immunological assays. They are needed to insure the reliability and accuracy of test equipment and methods and to insure reproducibility through time and from laboratory to laboratory. State and federal regulations which govern such assays often require the use of multi-level controls in order to demonstrate that equipment is performing properly over a range of values. In immunological assays, fresh normal cells have been the standard control cells for such equipment testing. In order to avoid the cost and expense of obtaining and maintaining fresh cells, various methods of preserving fresh cells have been evaluated. For example, U.S. Pat. No. 5,059,518 (the '518 patent) describes the use of lyophilized normal mammalian cells for use as control cells.

Abnormal blood cell samples have also been used as controls to confirm the presence of a disease or determine its stage, but their use has been restricted to fresh or fresh-frozen samples drawn from diseased patients. The supply of such samples is thus inherently restricted. Furthermore, since many of such blood samples are associated with infectious diseases, they are not amenable, for health and social as well as sometimes technical reasons, to large scale production and distribution, and they require special handling procedures. This invention describes an alternative to the use of such abnormal control cells through the use of normal control cell samples which have been modified to reflect the population or count of one or more specific cell types as present in the blood of a person evidencing a specific disease.

SUMMARY OF THE INVENTION

The invention provides for control cells which reflect a specific cell population in a blood sample of a mammal having a disease which manifests itself, among other ways, as a change in the type, number or physiochemical properties of cells present in blood, and a method of producing and preserving such control cells. The control cells reflect the abnormal extant state of a blood cell population arising from: (1) an increase or decrease in the number of cells of a specific type due to the presence of a disease, the increase or decrease being relative to the number of such cells in a normal blood sample; or (2) the presence of cells not normally found in a normal blood samples, such cells being different in size, shape or other physical characteristics, or having thereon molecules and/or antigentic sites not found on the normal cells. The control cells of the first type are prepared by depleting a blood sample of specific cells normally present in blood to less than normal levels or by adding such cells above the normal level present in blood, and subsequently preserving such samples. The control cells of the second type are prepared by the addition of cells not normally present in blood to a normal blood sample and subsequently preserving such sample.

BRIEF DESCRIPTION OF THE DRAWINGS

FIG. 7 graphically depicts the percentage decrease in CD4 cells as a normal cell sample is diluted with increasing volumes of a CD4 depleted sample.

FIG. 8 graphically depicts the change in CD4 cell count per cubic milliliter sample volume as a normal cell sample is diluted with increasing volumes of a CD4 depleted sample.

DETAILED DESCRIPTION OF THE INVENTION

Figure 1A:
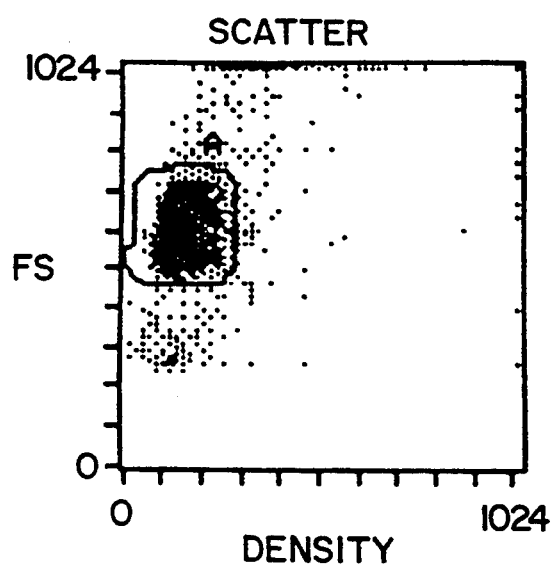
FIGS. 1 (a)–(d) represents a flow cytometric analysis of a normal blood sample in which the leukocytes have been conjugated with a PE (phycoerythrin) labelled anti-CD19 monoclonal antibody and a FITC (fluoroscein isothiocyanate) labelled anti-CD10 monoclonal antibody.

As used herein, the term "abnormal control cell sample" refers to a cell sample in which the population or count of cells, either total or a specific type, differs from that of a normal blood sample; or there is present in the abnormal blood sample cells which are not present in a normal blood sample. For example, normal values for the total leukocyte (white blood cell or WBC) count range from 4,300 to 10,800 per cu. mm. The normal values for the various cell types in the differential leukocyte count, are: segmented neutrophils=34–75%, band neutrophils=0–8%, lymphocytes=12–50%, monocytes=3–15%, eosinophils=0–5% and basophils=0–3% (The Merck Manual, 14th Ed., R. Berkow, ed (Merck Sharp & Dohme, Rahway, N.J. 1982), page 2182). In an abnormal blood sample, these values are different. For example, (1) in a sample from a patient suffering from chronic granulocytic leukemia, the WBC count may be elevated to range between 15,000 to 500,000 or high (ibid., page 1142); (2) a hemophiliac will have a mild to severe deficiency of factor VIII, which is identified as an antigen (ibid, pages 1127–1129); and (3) in a sample from a patient suffering from common acute lymphoblastic leukemia (CALL), cells will have a CD10 antigen not normally present which may be identified specifically by an anti-CD10 monoclonal antibody such as J5 (Coulter Corporation Hialeah, Fla).

The term "physiochemical properties" includes the antigenic characteristic of cells whether such characteristics are normally present or absent as the result of a disease.

The invention may be satisfied by embodiments in many different forms and in relation to different mammalian species. While the detailed examples described herein relate to humans and to analyses relating to AIDS and to CALL, they are to be considered exemplary of the principles of the invention and are not intended to limit the scope of the invention to such specific embodiments. Furthermore, while many of the molecular structures used to identify a type of cell are unique to humans and do not normally occur in other mammals, practice of the invention is not restricted to human control cell samples and a method of preparing the same. For example, control cell samples could be prepared for diagnosing feline leukemia virus or simian T-cell lymphotropic virus 1 (STLV-I), among others.

Abnormal control cells are usually associated with one of two conditions. In the first, there is an increase or a decrease in the population or count of a particular type of cells. For example, blood samples periodically taken from a HIV (AIDS) infected person will show a decrease in CD4 positive lymphocytes as the disease progresses. In the second, there appear cells that are not found in a normal blood sample. For example, the appearance of CD10 positive cells in the peripheral blood samples of patients suffering from Common Acute Lymphoblastic Leukemia [CALL; K. A. Foon et al., "Immunologic Classification of Leukemia and Lymphoma", Blood 68: 1–31 (1986)]. The immunological analysis of a peripheral blood sample for the various cell populations is performed, usually instrumentally, by associating the binding of specific monoclonal antibodies to specific molecular structures on or in a specific type of cell. For example, CD4 positive lymphocytes are identified by the binding of anti-CD4 monoclonal antibodies to an antigenic site or sites of a CD4 molecule. Several different molecular structures may have to be identified on a single cell in order to identify a particular type of cell or a particular type of cell associated with a specific disease. A broad class of cells may be increasingly divided into smaller and more specific subsets. In order to distinguish one broad class of cells within several broad classes and to further distinguish subsets of the selected broad class, different labels may be attached to the different monoclonal antibodies. For example, one may use, alone or in combination, radioactive element containing molecules, enzymes and dyes, especially fluorescent dyes, as such labels. Fluorescent dyes are preferred and examples of such dyes include fluorescein, fluorescein isothiocyanate (FITC), tetramethylrhodamine isothiocyanate (TRITC), phycoerythrin (PE or RD), phycoerythrin-Texas Red conjugates and allophycocyanin, among others.

In general, the method of preparing the control cells for which a decreased number of specific cells is important, comprises pooling normal, leukocyte rich, anticoagulated blood samples, lysing the red blood cells (RBCs) therein and washing the samples to remove lysis debris or removing RBCs by any other suitable procedure, for example, as described in U.S. Pat. No. 4,752,863, removing a specific cell type from the sample by use of a monoclonal antibody conjugated to a separable substrate such as glass, ceramic or polymeric beads, preferably magnetic beads, and adding back the removed cells to specific levels which may be indicative of various stages of the progression of a disease. The samples are then preserved for long term storage, for example, by lyophilizing the sample according to the procedures described in U.S. Pat. No. 5,059,518, whose teachings are incorporated herein by reference or by other suitable cell preservation techniques. The control cells thus produced have present a normal spectrum of leukocyte cells except for those specific, disease related cells whose number has been increased or decreased, or those specific disease related cells which have been added.

DESCRIPTION OF THE PREFERRED EMBODIMENTS

The following examples are given by way of illustration and are not to be taken as limiting the invention.

Patients having HIV exhibit decreased levels of CD4 (T4) cells in their blood. Since CD4 cells are important in combatting many of the secondary diseases which directly cause the death of a AIDS patient, assaying the CD4 population is indicative of the progress of the HIV infection and the ability of the patient to stave off secondary infections. While analysis of a patient's blood sample is absolutely necessary, it is desirous that the control samples used in the analysis be non-infectious so as to minimize accidental transmission of any disease.

EXAMPLE 1

Preparation of CD4 Depleted Normal Blood Cells for Use as AIDS Control Cells

A number of ACD (acid citrated dextrose) or CPD (citrated, phosphated dextrose) anticoagulated, leukocyte rich, normal blood packs are combined in a vessel to give a bulk leukocyte rich blood sample. The red blood cells in the sample are lysed using a 0.83 wt% ammonium chloride solution. After lysis, the leukocyte cells are washed a plurality of times with Hepes-saline-bovine serum albumin (HSB) solution. The leukocyte cells are then separated from the final wash and placed in a vessel with an isotonic 10% trehalose solution as a preservative medium. A portion of the leukocyte cells are reserved for later use. Separately, an anti-CD4 monoclonal antibody such as T4 (Coulter Corporation, Hialeah) is conjugated to magnetic beads by methods such as those described in U.S. Pat. No. 4 752 563 among others. The anti-CD4 conjugated magnetic beads are added to the washed leukocyte sample and mixed for about 30 minutes. The beads and cells attached thereto are then removed from the vessel using a magnetic device; for example, a hand held magnetic or a commercially available magnetic separator. The cells remaining in the vessel are centrifuged, the supernatant liquid is removed and the cells resuspended in an isotonic trehalose solution, preferably an isotonic 10% trehalose solution, as preservation medium. Samples containing different numbers of CD4 cells are then prepared by mixing the CD4-depleted sample with varying quantities of the reserved leukocyte cells or normal, red blood cell free leukocyte cells from other samples with known number of CD4 cells. For example:

Level 1 CD4 cells: Equal volumes of the reserved leukocytes and the CD4 depleted leukocytes are mixed to yield a sample having 50% of the CD4 cells present in the original normal pooled blood sample.

Level 2 CD4 cells: Three volumes of the reserved leukocytes and one volume of CD4 depleted leukocytes are mixed to yield a sample having 25% of the CD4 cells present in the original pooled blood sample.

Level 3 CD4 cells: Nine volumes of the reserved leukocytes and one volume of CD4 depleted leukocytes are mixed to yield a sample having 10% of the CD4 cells present in the original pooled blood sample.

FIGS. 7 and 8 graphically present CD4 control cells prepared as described. FIG. 7 depicts the change in the percent positive cells as a normal CD4 containing sample is diluted with increasing amount of CD4 depleted blood. FIG. 8 depicts the change in the absolute number of CD4 positive cells per cubic millimeter sample as dilution increases.

Alternatively, additional normal ACD or CPD anticoagulated, leukocyte-rich blood packs are pooled, the red blood cells are lysed and the leukocytes are washed as previously described herein. The number of CD4 cells present in the pooled sample may be determined by flow cytometry using fluorescently labelled T4 monoclonal antibody. Aliquots of this pooled, CD4 containing sample may then be mixed with varying amounts of CD4 depleted leukocytes to prepare control cell samples having varying concentrations of CD4 cells.

EXAMPLE 2

Preparation of CD10 (CALLA) Augmented Control Cells

A plurality of normal ACD or PCD anticoagulated, leukocyte-rich red blood packs are pooled and the red blood cells then lysed using an 0.83 wt% ammonium chloride solution. After lysis, the leukocyte cells are washed a plurality of times with HSB. The leukocyte cells are then separated from the final wash and placed in a vessel with isotonic 10% trehalose solution as the preservative medium. Cultured CALLA (CD10 positive, common acute lymphoblastic leukemia antigen) positive cells are separately prepared using commercially available CALLA positive cells, an American Type Culture Collection (ATCC) CALLA sample, or cells from other sources. The cells used here are from the ATCC, deposit number CRL 1596. The cultured CD10+ cells are then added in different amounts to aliquots of normal leukocyte cells in the preservative solution.

EXAMPLE 3

Lyophilization of Stabilized Normal Cells for Use as Non-infectious Diseased Cell Controls The control cells prepared as described in Examples 1 and 2 are lyophilized in accordance with U.S. Pat. No. 5,059,518 whose teachings are incorporated herein by references. Specifically the Level 1, 2 or 3 CD4 control cells or CALLA control cells suspended in the isotonic 10% trehalose solution are placed in 300 μL lyophilization vials, the vials capped and cooled to 4° C., and then agitated to assure even and smooth dispersion of cells before the vials are placed in a freezer at about −70° C. for at least one hour. After the freezing time, the vials are immediately placed in a lyophilizer for a period of about 15 hours. The lyophilized vials are removed from the lyophilizer after the expiration of the fifteen hour cycle and stored at refrigeration temperatures of between 2°-8° C. The control cells may be stored for six months or more. The lyophilized cells may be reconstituted by filling the lyophilization vial to its 300 μL volume with deionized or distilled water. For conducting a control assay on a flow cytometer, the resuspended reconstituted cells are stained, or otherwise labelled or marked, and thereafter analyzed by standard flow cytometer procedures. The resuspended cells can also be used in other types of assays or other suitable diagnostic protocols.

Figure 1B:
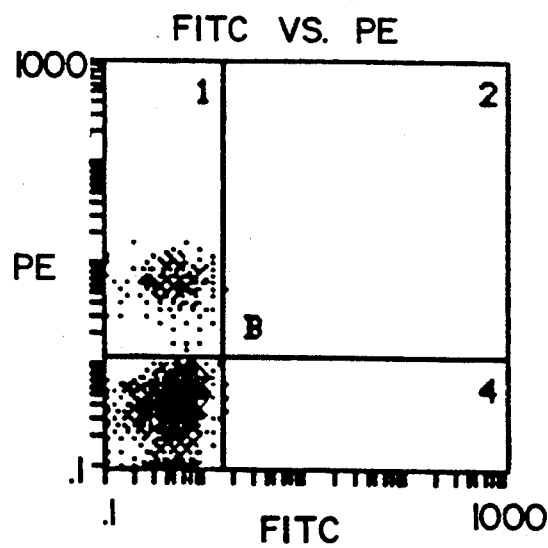
Figure 1C:
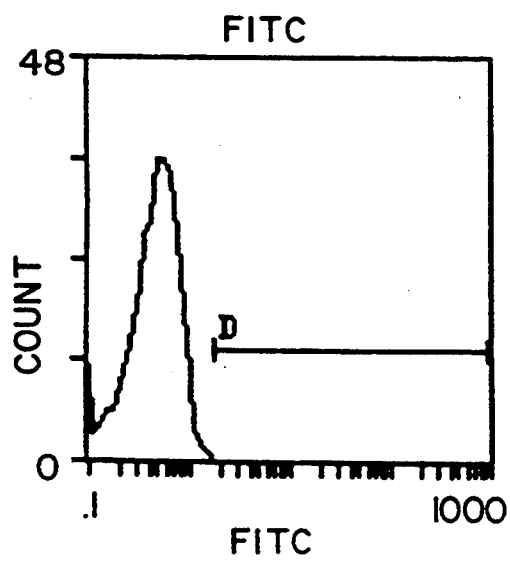
Figure 1D:
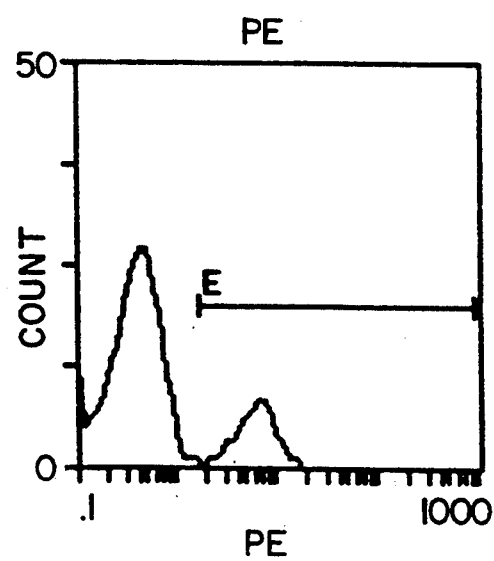
Figure 2A:
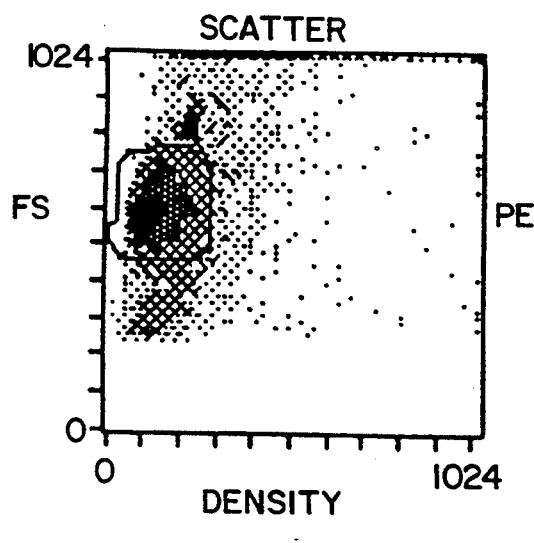
FIGS. 2 (a)–(d) represent a flow cytometric analysis of normal blood sample containing added CD10 positive cells.
Figure 2B:
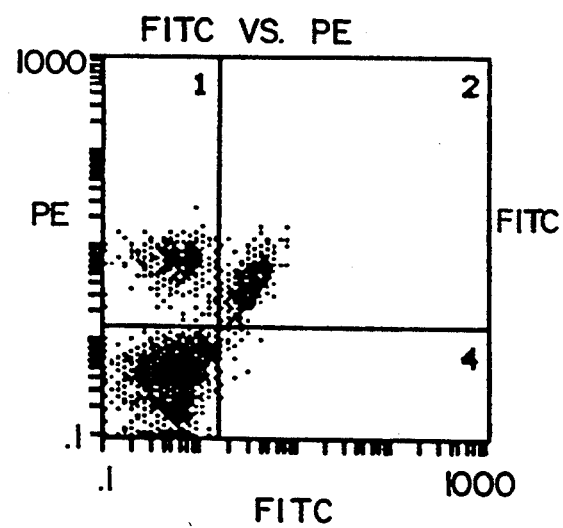
Figure 2C:
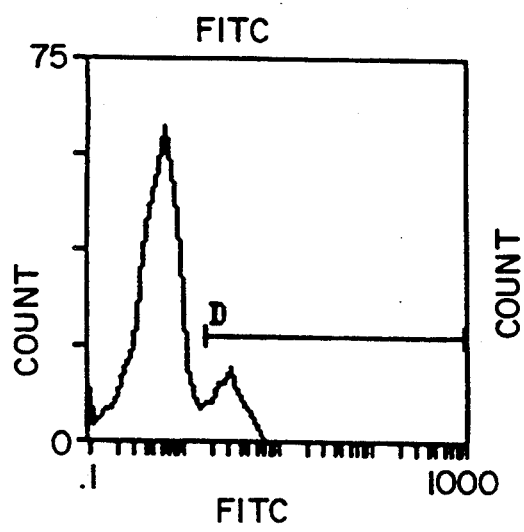
Figure 2D:
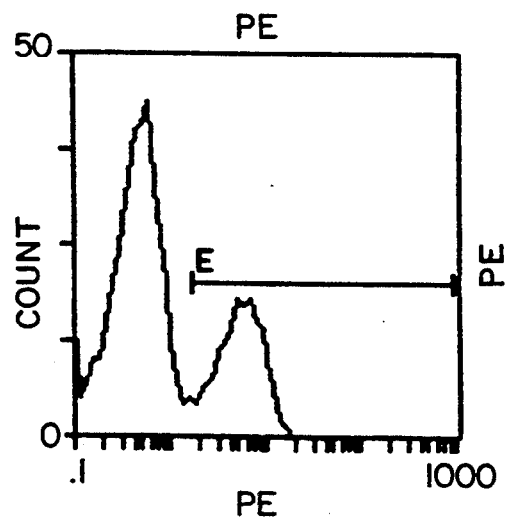
Figure 3A:
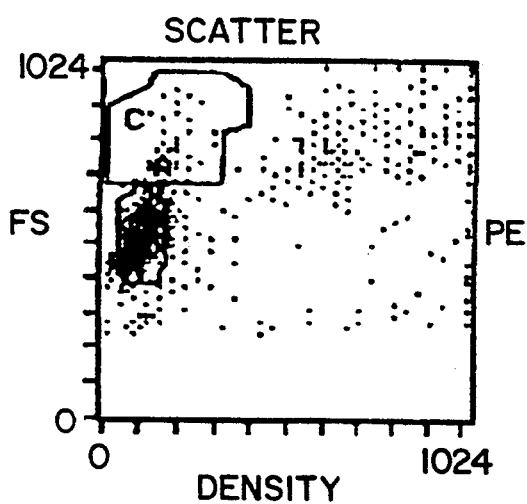
FIGS. 3 (a)–(d) represent a flow cytometric analysis of a blood sample from a patient having common acute lymphoblastic leukemia.
Figure 3B:
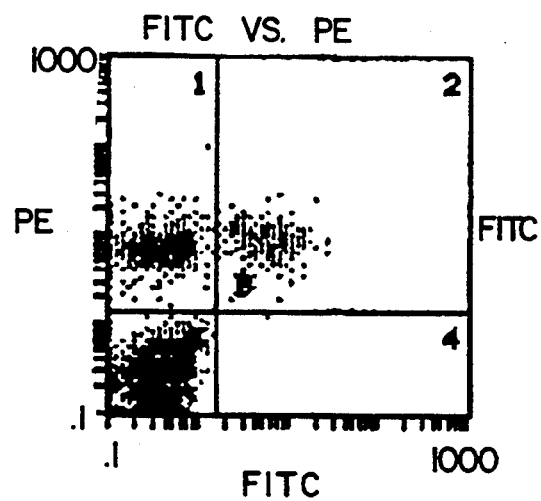
Figure 3C:
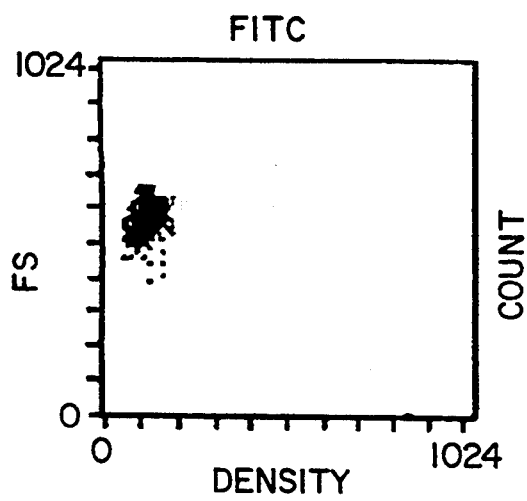
Figure 3D:
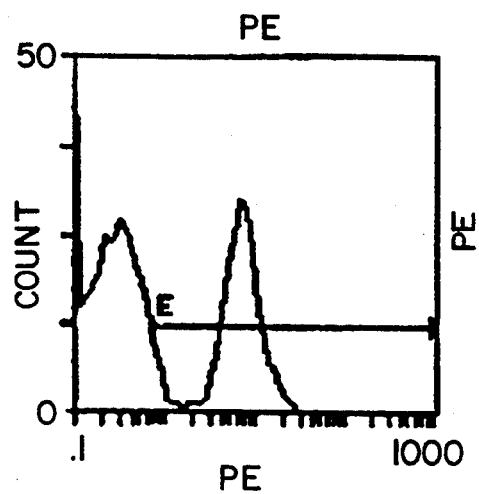

FIGS. 1, 2 and 3, (a)-(d) compare normal cells (FIG. 1) with patient cells (FIG. 3) and control cells prepared according to the invention (FIG. 2). These figures indicate that the assay is able, using the control cells, to detect the abnormal CD10+ and CD19+ cells which would be present in a diseased patient blood sample.

Figure 4A:
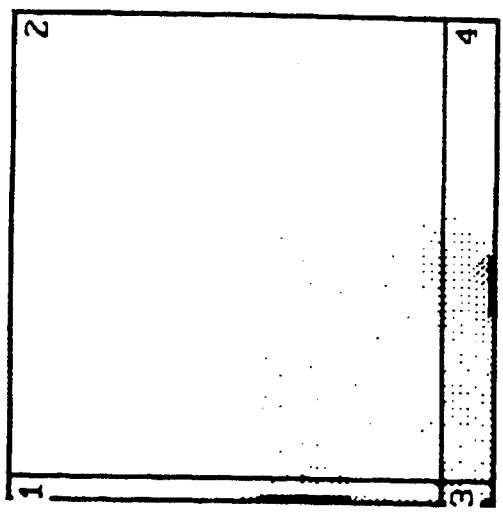
FIGS. 4 (a)–(d) represents a flow cytometric analysis of lymphocytes from a normal blood sample.
Figure 4B:
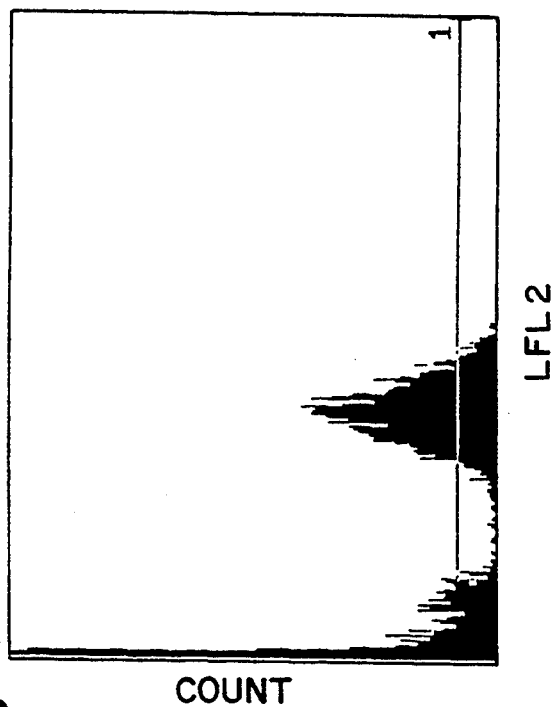
Figure 4C:
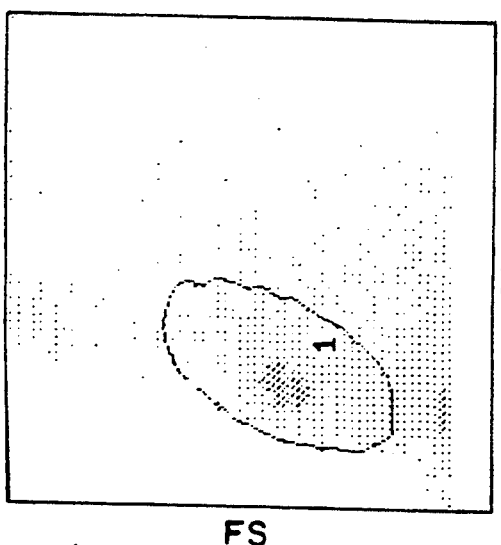
Figure 4D:
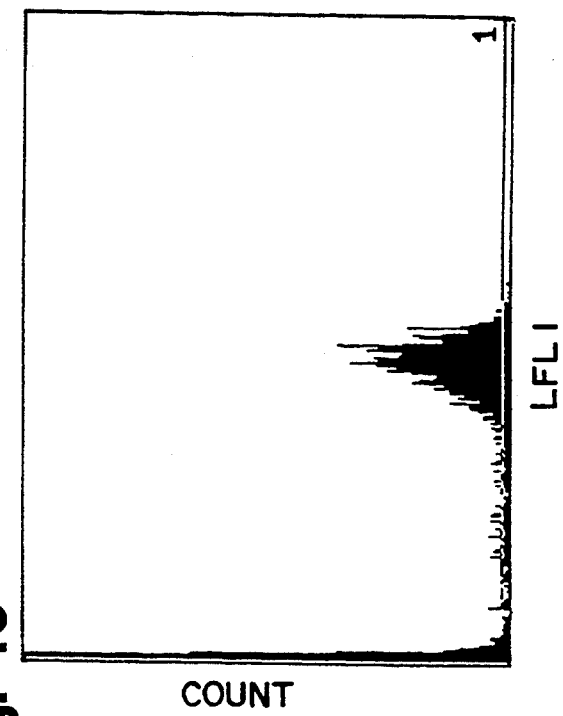
Figure 5A:
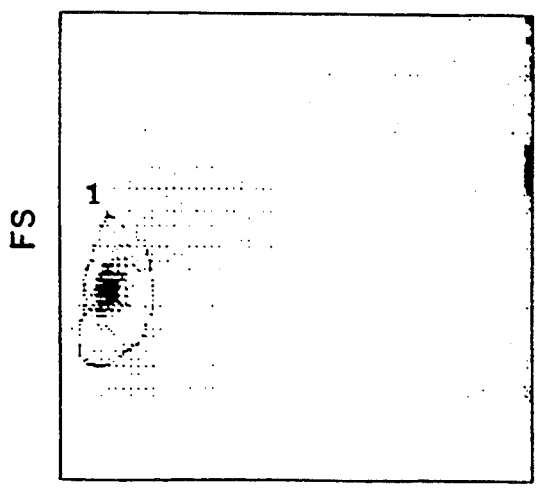
FIGS. 5 (a)–(d) represents a cytometric analysis of lymphocytes a blood sample from an AIDS patient.
Figure 5B:
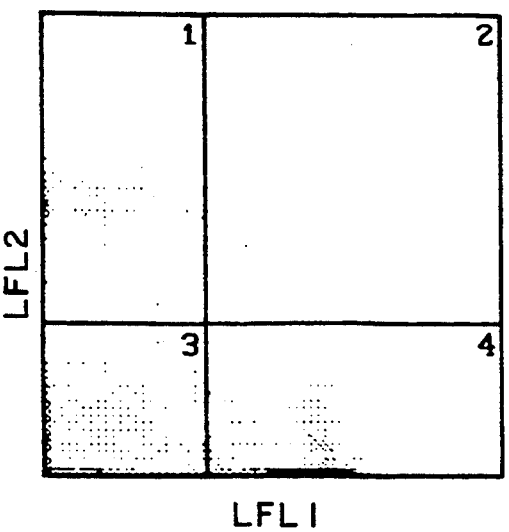
Figure 5C:
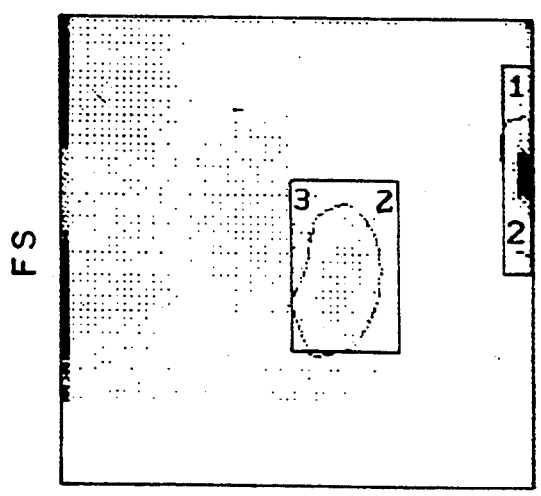
Figure 5D:
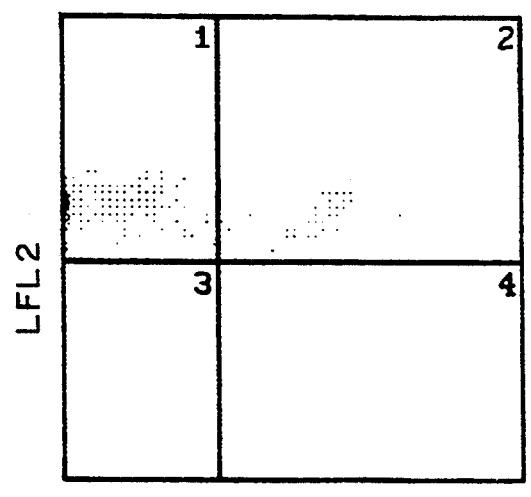
Figure 6A:
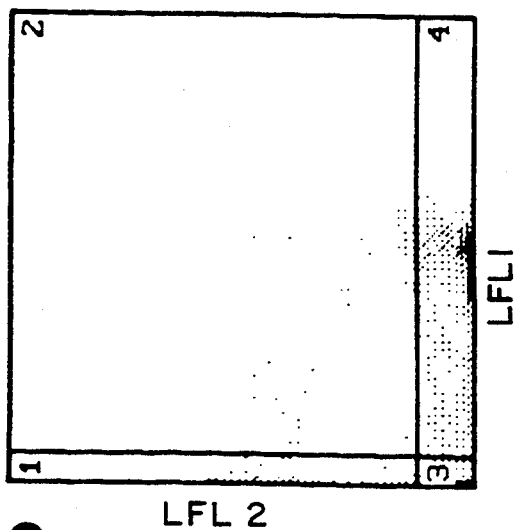
FIGS. 6 (a)–(d) represents a cytometric analysis of lymphocytes from which CD4 cells have been depleted according to the invention.
Figure 6B:
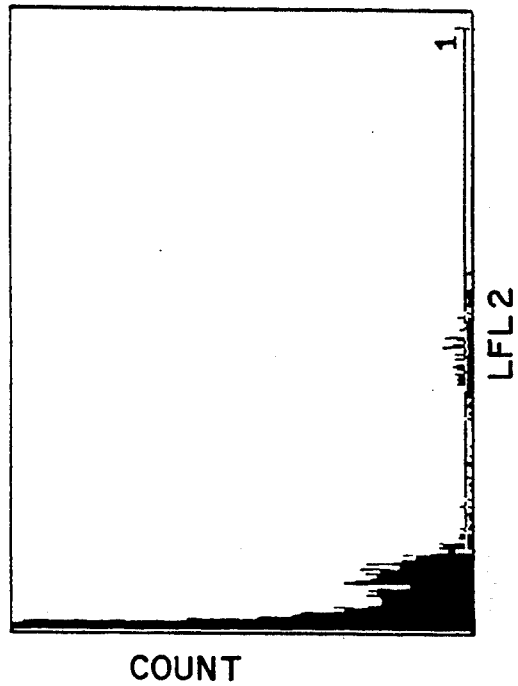
Figure 6C:
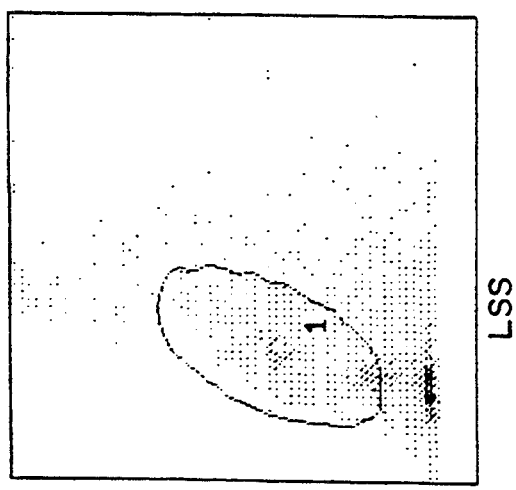
Figure 6D:
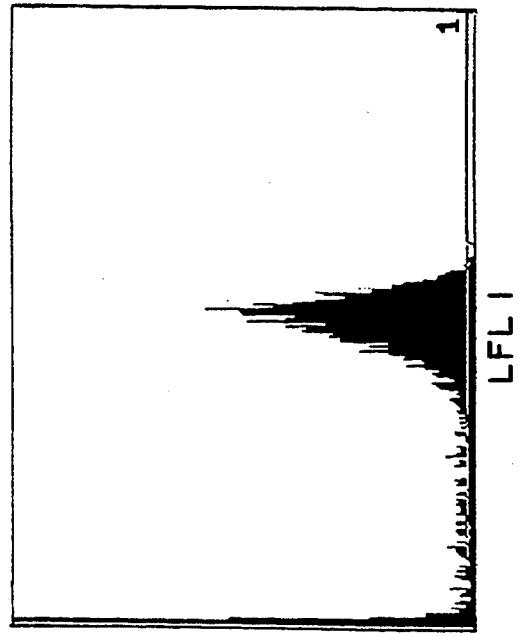

FIGS. 4, 5 and 6, (a)-(d), indicate that the assay is able to detect the low number of CD4+ cells that would be seen in an AIDS patient. In FIG. 4, Quad 1 represents CD4+ cells as present in a normal blood sample. In FIG. 5, Quad 1 represents the depleted number of CD4+ cells as seen in an AIDS patient. In FIG. 6, Quad 1 shows that the equipment is able to detect the depleted CD4+ as represented by the depleted control cells of the invention.

We claim:

1. Control cells comprising leukocyte cells which have been lyophilized with an isotonic trehalose solution, said control cells reflecting the type, number and physiochemical properties of leukocyte cells in the blood of a mammal having a disease, which disease has as one of its manifestations a change in the type, number and physiochemical properties of the leukocyte cells in the blood of said diseased mammal, said control cells further identified as being normal mammalian leukocyte cells in which:

(a) at least one specific subset of normal leukocyte cells has been artificially depleted to a count below that present in a normal leukocyte cell sample, or
   (b) at least one specific subset of normal leukocyte cells which has been artificially increased to a count above that present in a normal leukocyte cell sample, or
   (c) at least one specific subset of cells, not present in a normal leukocyte cell sample, has been added to said normal leukocyte sample, in order that the control cells which result from the lyophilization of (a), (b) or (c) have a leukocyte cells distribution similar to that of the diseased mammal.

2. The control cells according to claim 1 in reconstituted form wherein said cells are useful as biological controls in immunological assays.

3. Control cells in accordance with claim 1 in which said cells are derived from normal human peripheral blood cells.

* * * * *